(12) United States Patent
Dosaka et al.

(10) Patent No.: US 6,956,229 B2
(45) Date of Patent: Oct. 18, 2005

(54) FLUORESCENCE READER WHEREIN UNIFORM FLUORESCENCE MEASUREMENT IS ACCOMPLISHED REGARDLESS OF THE STATE OF THE MEASUREMENT OBJECT

(75) Inventors: Shinichi Dosaka, Tsukui-gun (JP); Seiji Kondo, Hachioji (JP); Sachiko Karaki, Hino (JP); Yoko Ohashi, Ithaca, NY (US)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/724,242

(22) Filed: Nov. 28, 2003

(65) Prior Publication Data

US 2004/0130715 A1 Jul. 8, 2004

Related U.S. Application Data

(63) Continuation of application No. PCT/JP02/05280, filed on May 30, 2002.

(30) Foreign Application Priority Data

May 30, 2001 (JP) ........................................ 2001-163394

(51) Int. Cl.$^7$ .............................................. G01N 15/06
(52) U.S. Cl. .................................... 250/573; 250/459.1
(58) Field of Search ............................. 250/573, 458.1, 250/459.1

(56) References Cited

U.S. PATENT DOCUMENTS

| | | | |
|---|---|---|---|
| 5,296,700 A | | 3/1994 | Kumagai |
| 5,523,573 A | * | 6/1996 | Hanninen et al. ......... 250/459.1 |
| 5,793,049 A | * | 8/1998 | Ballard .................... 250/458.1 |
| 6,238,874 B1 | * | 5/2001 | Jarnagin et al. ........... 435/7.21 |

FOREIGN PATENT DOCUMENTS

| | | |
|---|---|---|
| JP | 5-72481 A | 3/1993 |
| JP | 8-43739 A | 2/1996 |
| JP | 2002-14044 A | 1/2002 |

* cited by examiner

Primary Examiner—Thanh X. Luu
(74) Attorney, Agent, or Firm—Frishauf, Holtz, Goodman & Chick, P.C.

(57) ABSTRACT

A fluorescence reader of the present invention detects fluorescence from a sample present on a carrier or in a solution, and the fluorescence reader includes a light source which radiates parallel light, a projection lens which converges the light from the light source, an objective lens which irradiates the sample with the light converged in a rear-side focal position, an image forming lens which forms fluorescence emitted from the sample and passed through the objective lens into an image, a light receiving pinhole disposed in an image forming position of the image forming lens, and detector which detects the fluorescence passed through the light receiving pinhole.

5 Claims, 4 Drawing Sheets

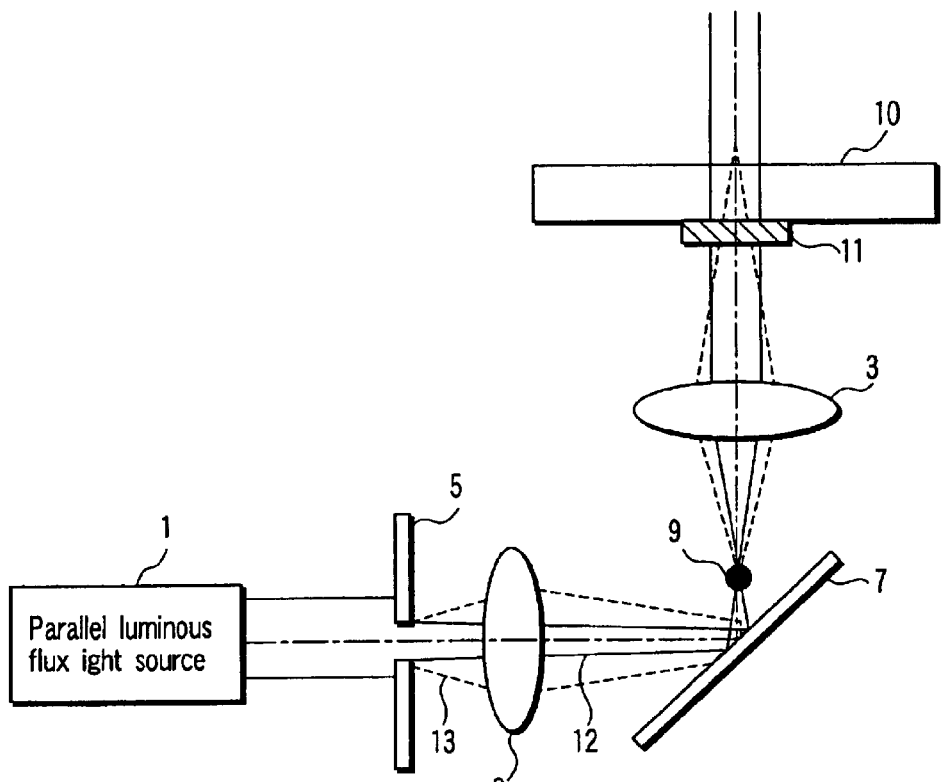
F I G. 2
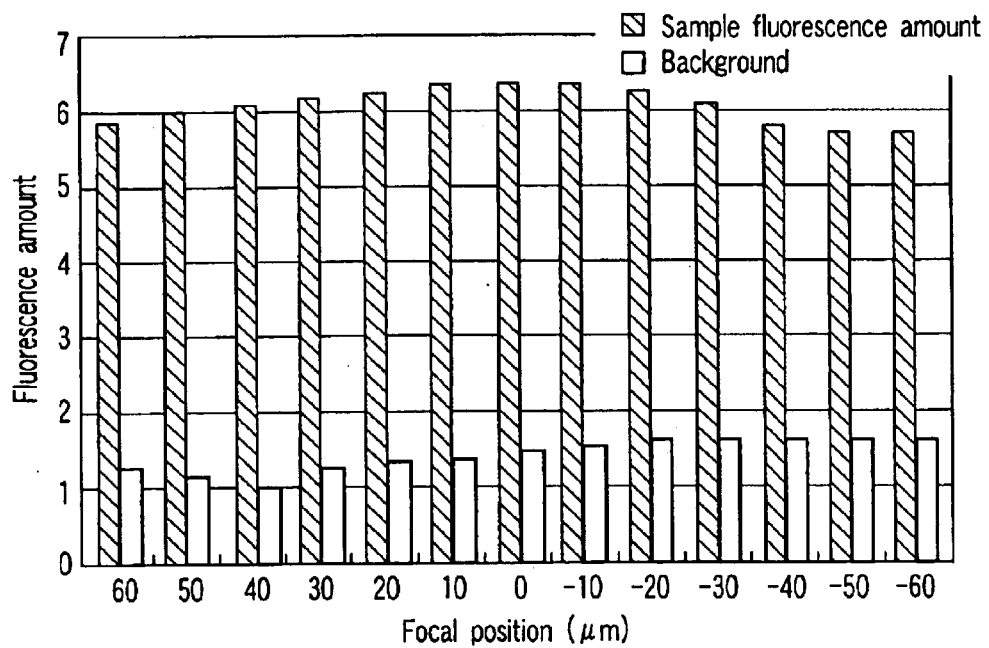
F I G. 3

FLUORESCENCE READER WHEREIN UNIFORM FLUORESCENCE MEASUREMENT IS ACCOMPLISHED REGARDLESS OF THE STATE OF THE MEASUREMENT OBJECT

CROSS-REFERENCE TO RELATED APPLICATIONS

This is a Continuation Application of PCT Application No. PCT/JP02/05280, filed May 30, 2002, which was not published under PCT Article 21(2) in English.

This application is based upon and claims the benefit of priority from the prior Japanese Patent Application No. 2001-163394, filed May 30, 2001, the entire contents of which are incorporated herein by reference.

BACKGROUND OF THE INVENTION

1. Field of the Invention

The present invention relates to a fluorescence reader which detects fluorescence from a sample present on a carrier or in a solution.

2. Description of the Related Art

This type of reader includes a reader for measuring fluorescence of a so-called DNA chip or DNA micro array in which a complementary sequence (hereinafter referred to as a probe) is constituted in a solid phase on a carrier of glass, silicon, or plastic especially in a part of a peculiar sequence of a nucleic acid which is a detection target. In this reader, each probe is labeled with the fluorescence to measure the fluorescence. However, it is known that the quantity of fluorescence to be detected here is very small as compared with that of fluorescence for another cell or tissue which is a detection object.

Therefore, the quantity of fluorescence needs to be detected with high sensitivity. For this, the principle of a fluorescence reader is roughly divided into:

(1) a confocal/photomultiplier tube/scanning system; and (2) a cooling CCD system. These have the following characteristics.

(1) This system of a fluorescence reader carries out scanning by a confocal laser system, and is used mainly in an application of detecting a coupling reaction of the nucleic acid on the glass carrier. In the confocal system, noise by a disturbance light is removed, and high measurement performance is realized, but the focal depth is very shallow. The focal depth of a general confocal laser system depends on the NA of an objective lens, and is obtained by the following equation.

$$\text{Focal depth} = (0.6 \times \text{wavelength})/(\text{NA})^2$$

For example, when a laser having a wavelength of 632 nm is used to use a lens having an NA of 0.3, the focal depth is about 4 $\mu$m from the above equation. In an optical system having such a narrow depth, when the fluorescence is focused, clear fluorescent photometry is obtained without any noise. However, when a focal point deviates, the correct quantity of fluorescence cannot be measured. When the fluorescence is focused inside glass, self fluorescence of glass is picked up, and the background brightens. Therefore, the fluorescence is easily influenced by distortion, deflection, and the like on the side of a chip or array, and there is a fear that a uniform fluorescent screen image is not easily obtained with respect to a chip or array front plane.

Moreover, in this type of latest reader, an auto-focusing function which is tuned in the scanning is taken in, and an improvement is made so as to obtain the uniform fluorescent screen image, but there are disadvantages of enlargement and price rise of the reader.

(2) In this type of fluorescence reader, a halogen lamp is used in a light source, and a cooling CCD is used. The reader is used in the application of detecting the coupling reaction of the nucleic acid on the micro array of the glass carrier prepared using a micro array system. In this system, as compared with the system (1), a broad range can be measured at once, and a read time is short. When an exposure time is changed, samples intense to weak in the fluorescence can broadly be handled. Furthermore, there are characteristics that a filter for an exciting light is changed, and accordingly the exciting light is obtained in accordance with a fluorescent material for use.

However, in actual measurement, sensitivity of principle is inferior to that of the system (1), and there is a disadvantage that the system is insufficient in SNP dyping or gene expression frequency analysis measurement which requires high-sensitivity analysis.

(1). At present, for the chip or micro array for use mainly in a field of molecular biology, the materials of the carrier are various such as a glass plate, silicon plate, and porous filter formed of nylon or nitrocellulose. In any of these materials, subtle distortion, deflection, and self fluorescence exist. Therefore, when a very small amount of fluorescence is to be measured on the surfaces of these materials, in the above-described conventional art, uniform fluorescent photometry cannot be performed with respect to the whole measurement surface because of the distortion, and the like.

(2). Prior arts described above in (1), (2) have problems that (1) since the confocal laser system is used, exact measurement is possible at the time of focusing, but read sensitivity drops at the time of non-focusing, and that (2) the read sensitivity is low in the CCD system because of a sensitivity difference and photometry range difference between the photomultiplier tube and CCD, respectively. In general, an exciting light intensity needs to be raised in order to detect the fluorescence with the high sensitivity, but especially when the fluorescent material is an organic material, there is a problem that the material is remarkably deteriorated with an increase of the exciting light intensity.

(3). In order to overcome the problems (1), (2) described above in (2), in the latest technology, attempts have been made to adopt an auto focus system, or to increase the number of applied laser beams. Accordingly, control measurement is performed to make corrections. However, these measures tend to enlarge the reader and to raise prices. Moreover, the carrier has protrusions such as partition walls depending on the shape of the carrier, and the optical systems such as an auto focus cannot be added in some case.

(4). In the conventional reader, when the focal point is moved only by several micrometers, a fluorescence read amount largely changes, the amount of noises largely increases/decreases, and it is not thus easy to set measurement conditions.

An object of the present invention is to provide a fluorescence reader in which the uniform fluorescence measurement is carried out regardless of a state of the measurement object, the very small amount of fluorescence can be detected with the high sensitivity, the setting of the measurement conditions is facilitated, and miniaturization of the reader is achieved.

BRIEF SUMMARY OF THE INVENTION

According to the present invention, there is provided a fluorescence reader which detects fluorescence from a sample existing on a carrier or in a solution, the fluorescence reader comprising: a light source which radiates parallel light; a projection lens which converges the light from the light source; an objective lens which irradiates the sample with the light converged in a rear-side focal position; an image forming lens which forms fluorescence emitted from the sample and passed through the objective lens into an image; a light receiving pinhole disposed in an image forming position of the image forming lens; and detector which detects the fluorescence passed through the light receiving pinhole.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a diagram showing a partial configuration of an optical system according to the embodiment of the present invention;

FIG. 3 is a diagram showing a change of a fluorescent amount with respect to a focal position according to the embodiment of the present invention;

DETAILED DESCRIPTION OF THE INVENTION

An embodiment of the present invention will hereinafter be described with reference to the drawings.

Figure 1:
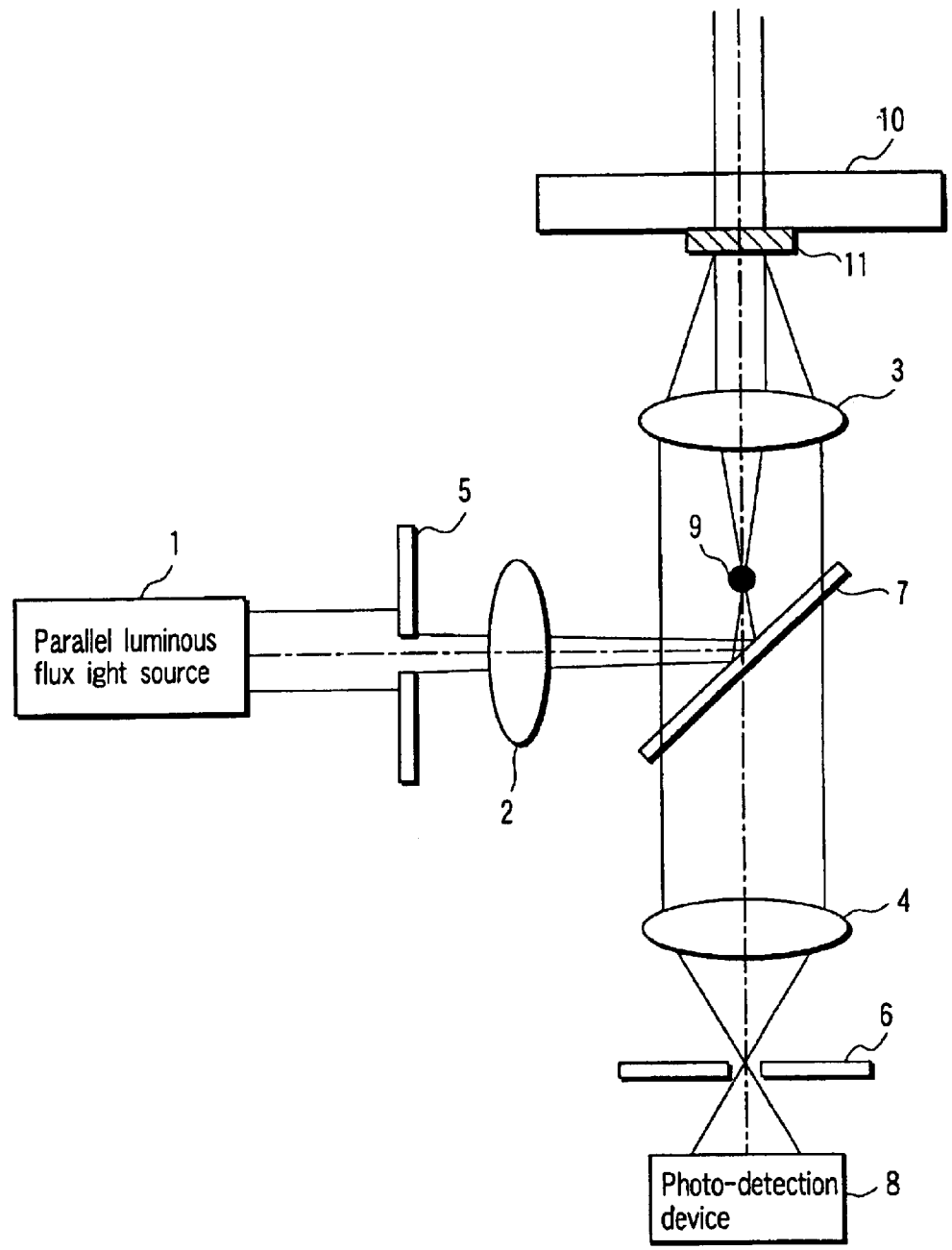
FIG. 1 is a diagram showing an optical system of a very small amount fluorescence reader according to an embodiment of the present invention.

FIG. 1 is a diagram showing an optical system of a very small amount fluorescence reader according to the embodiment of the present invention, and FIG. 2 is a diagram showing a partial configuration of FIG. 1. This very small amount fluorescence reader measures and quantifies fluorescence from a sample, which exists on a carrier or in a solution.

As shown in FIG. 1, an excitation pinhole 5, a projection lens 2, and a wavelength selection element (dichroic mirror) 7 are disposed on an optical path of a parallel luminous flux light source 1. It is to be noted that the excitation pinhole 5 is formed of a plate member in which a pinhole is disposed, and disposed in a front-side focal position of the projection lens 2. An objective lens 3 and a sample (probe) 11 held by a carrier 10 are disposed on a reflected light path of the wavelength selection element 7. An image forming lens 4, a light receiving pinhole 6, and a photo-detection device 8 are disposed on a transmitted light path of the wavelength selection element 7. It is to be noted that the light receiving pinhole 6 is formed of the plate member in which the pinhole is disposed, and disposed in a rear-side focal position of the image forming lens 4.

A part of a parallel light radiated from the parallel luminous flux light source 1 passes through the pinhole of the excitation pinhole 5, and is reflected by the wavelength selection element 7 via the projection lens 2, and converged in the vicinity of a rear focal position 9 of the objective lens 3. Subsequently, the sample 11 on the carrier 10 (or in a solution) is irradiated via the objective lens 3 in a telecentric manner. Fluorescence emitted from the sample 11 is transmitted through the wavelength selection element 7 via the objective lens 3, formed into an image by the image forming lens 4, passed through the pinhole of the light receiving pinhole 6 disposed in the image forming position, incident upon the photo-detection device 8, and detected.

In this manner, in the configuration of the present embodiment, the excitation pinhole 5 is disposed in the front-side focal position of the projection lens 2, so that a size of the image formed by the projection lens 2, objective lens 3, and image forming lens 4 is substantially equal to that of the light receiving pinhole 6.

The configuration of the present embodiment is similar to that of the optical system called "Koana-Naora system", but is characterized in that an exciting light is used in telecentric illuminating. Concretely, a parallel luminous flux is shaped by the excitation pinhole 5, and converged as a primary pinhole image in the pupil position 9 of the objective lens 3 by the projection lens 2 so as to form the exciting light with which the sample 11 is irradiated into the parallel luminous flux which has a certain sectional area. At this time, as shown in FIG. 2, a diffracted light 12 generated in the excitation pinhole 5 forms a secondary pinhole image on the surface of the sample 11. Since the focal position of the sample 11 can be known by this secondary pinhole image, focal adjustment can exactly be carried out.

The fluorescence excited by the exciting light and emitted from the sample 11 forms a secondary plane luminous flux, passes through the objective lens 3 again, and forms a tertiary pinhole image in the rear focal position of the image forming lens 4. There is an advantage that the light receiving pinhole 6 including the pinhole having a size substantially equal to that of the tertiary pinhole image is disposed and this prevents the fluorescence or a disturbance light emitted from a plane other than that of the sample 11 irradiated with the exciting light from reaching the photo-detection device 8.

Additionally, when the carrier has a self fluorescence, there is a problem that the self fluorescence is picked up by a large focal depth of the optical system in the present embodiment as described later. This is because the pinhole of the light receiving pinhole 6 disposed before the photo-detection device 8 is much larger than that for use in a general confocal optical system. Even in the general confocal optical system, the pinhole can be enlarged to increase the focal depth, but in this case, the advantage of the confocal optical system is eliminated.

FIG. 3 is a diagram showing a change of a fluorescent amount with respect to the focal position. In the present embodiment, since the fluorescence is emitted from a plane light source (sample 11), the focal depth is equal to that of a general optical microscope. Therefore, it is possible to solve a problem that fluorescent data easily becomes non-uniform by an influence of distortion or deflection of a chip or a micro array, and a problem that it is difficult to set measurement conditions such as focusing, which have heretofore been problems. However, if the carrier has the self fluorescence, a background noise is made, and the image entirely brightens.

Additionally, a quantity of light of the background noise indicates a substantially constant value regardless of the focal position as shown in FIG. 3. Therefore, the quantity of light of the background noise is measured beforehand in a portion in which there is not any sample 11 in the vicinity of the sample 11, the quantity of light is subtracted from the measured fluorescent amount of the sample, and accordingly it is possible to measure an exact fluorescent amount of the sample. Alternatively, when a material or shape of the carrier 10 is constant to some degree regardless of the sample, a background noise amount may be determined beforehand, and the amount may uniformly be subtracted from the measured fluorescent amount of the sample.

Moreover, in the present embodiment, the diffracted light 12 generated in the excitation pinhole 5 forms the secondary pinhole image on the sample 11 plane. Accordingly, the objective lens 3 can easily be focused onto the sample 11 plane. Usually, when the sample plane is irradiated with the exciting light as the parallel luminous flux, a problem that the focusing is difficult is considered, but this problem is also solved in the present embodiment. Furthermore, in the present embodiment, without adding auto-focus mechanisms, an effect of the focusing is obtained, and therefore a small-sized low-cost reader can be realized.

Furthermore, since the exciting light onto the sample 11 is the parallel luminous flux having the certain sectional area, an exciting light intensity per unit area is remarkably low as compared with that of the confocal optical system, and a dyestuff material can be inhibited from being deteriorated. Accordingly, the exciting light intensity can be raised as compared with the confocal optical system in the same degree of permissible deteriorated state. Since the fluorescent amount increases, it is also possible to raise sensitivity.

In the optical system of the present embodiment, the sectional area of the parallel luminous flux formed into the image on the sample 11 plane can freely be changed by the pinhole shape of the excitation pinhole 5, and a combination of a focal distance of the projection lens 2 with that of the objective lens 3. Therefore, when the excitation pinhole 5 is disposed in consideration of a parallel luminous flux diameter of the sample plane and a magnification of the optical system, it is possible to freely change a resolution of measurement while maintaining the above-described effect.

Moreover, when the size of the pinhole of the light receiving pinhole 6 is set to be larger than that of the tertiary pinhole image, it becomes easy to detect a total fluorescent amount from the sample 11 in the photo-detection device 8. In this case, a photometry interval at the time of measurement performed while scanning the sample 11 is shortened, three states repeatedly occur with relationships: a photometry region of the photo-detection device 8 and the sample 11 (a) do not overlap; (b) partially overlap; and (c) completely overlap with each other.

Here, in the completely overlapped state (c), even when the sample 11 is in any position within the photometry region, the fluorescent amount from the sample 11 measured by the photo-detection device 8 is constant. Therefore, when a profile of the measured fluorescent amount is analyzed, it is possible to easily grasp the state (c). When a plurality of fluorescent amounts measured in the state (c) are averaged, it is possible to enhance an SN ratio.

Conversely, when the size of the pinhole of the light receiving pinhole 6 is set to be smaller than that of the tertiary pinhole image, or when the pinhole is formed in a rectangular shape, the fluorescence only from a part of the sample 11 can be measured. Therefore, when the fluorescence is successively scanned and measured, a fluorescent distribution of the sample 11 can be formed into the image, and analyzed. As described above, the sizes and shapes of the pinholes are changed in accordance with the state of the sample 11 or measurement purpose, and the excitation pinhole 5 and light receiving pinhole 6 can properly be used.

A main measurement object in the present embodiment is one or more immobilized nucleic acids which constitute the sample 11 (probe) on the carrier 10, and a fluorescent dyestuff is coupled with a reagent peculiarly coupled with the nucleic acid. Therefore, by the detection of the fluorescence from the sample 11, it is judged whether or not a targeted nucleic acid is present. When the acid is present, the fluorescent amount can be measured.

However, the nucleic acid immobilized on the carrier 10 has a certain area usually of about 3 $\mu m^2$ to 3 $mm^2$, and this sample 11 is not necessarily uniformly immobilized. When the sample is nonuniformly fixed, the fluorescent amount emitted from the same type of sample also becomes nonuniform. Therefore, in order to measure an exact fluorescent amount, it is necessary to finely scan the whole sample 11, further calculate the nonuniform fluorescent image, and obtain the exact fluorescent amount. However, when the sample is precisely/minutely scanned, the scanning requires much time, and efficiency is deteriorated.

To solve the problem, in the present embodiment, the size of the pinhole of the light receiving pinhole 6 is set to be slightly larger than that of the tertiary pinhole image, the whole fluorescent amount is measured at once, and the scanning is accordingly simplified. In order to distinguish a plurality of immobilized samples 11 from one another, the samples are arranged at certain intervals on the carrier 10 to form a specimen in some case. In this case, after irradiating only the position of the sample 11 with the exciting light to measure a very small amount of fluorescence, the specimen is moved by the certain interval together with the carrier 10 to measure the next sample 11. When this is repeated, it is also possible to further accelerate the scanning with respect to a plurality of samples 11.

Moreover, the parallel luminous flux light source 1 usable in the present embodiment is not limited, but a frequently used light source is a laser source. The photo-detection device 8 is not limited either, and a photo-multimeter, an avalanche photodiode, and the like are well used to perform high-sensitivity detection. Also the wavelength selection element 7 is not limited as long as the exciting light can be separated from the fluorescence, but the dichroic mirror is well used. Moreover, even when a telecentric optical system does not necessarily include an exact configuration, the above-described characteristics can be obtained. Therefore, the system may be configured so as to prevent the parallel luminous flux from being converged in a range (about ±5 $\mu m$) in the vicinity of the sample 11. In this case, the size (width) of the parallel luminous flux can be set to 3 $\mu m$ to 200 $\mu m$, but in actual an appropriate size is 5 $\mu m$ to 50 $\mu m$.

Moreover, in the present embodiment, even when the sample 11 is attached onto either upper or lower side of the carrier 10, but when the objective lens 3 whose focal length is corrected by the thickness of the carrier 10 is used, the photometry is possible. This handling is also preferable in a case where the carrier 10 including high partition walls is used and the sample is attached on a side on which the partition walls are formed.

EXAMPLE

An example of the present invention will hereinafter be described.

In the present example, the optical system shown in FIG. 1 was used to configure a very small amount fluorescence reader. For the sample, single-strand DNA including 19 bases was dropped as the probe onto a commercial slide glass (manufactured by Matsunami Glass Co., Ltd.) in two concentrations of 100 nM and 10 nM. The dropped and dried probe had a size of about 350 µm.

With 3' terminals of single-strand DNA with 100 bases including a sequence complementary with the DNA of the probe, a specimen material labeled with a fluorescent dye-stuff (CY3 manufactured by Amasham Pharmacia Biotech Co., Ltd.) was reacted together with the slide glass on which the probe was fixed at a temperature of 60° C. for one hour. After the reaction, the slide glass cleaned with pure water and dried was measured.

Figure 4:
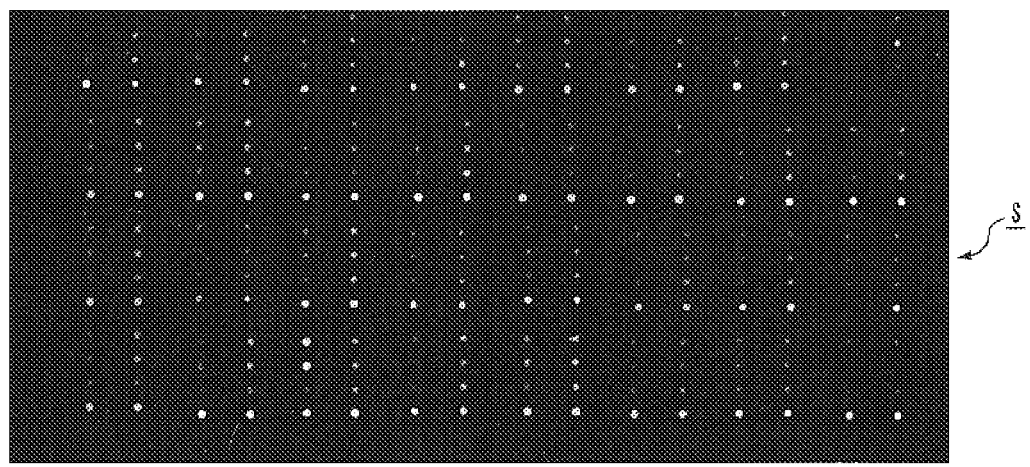
FIG. 4 is a photograph showing a measurement result according to an example of the present invention.

FIG. 4 is a photograph showing a measurement result of the present example. In the present example, a portion having a width of 20 mm and length of 60 mm in a slide glass S onto which the probe is fixed is measured. As shown in FIG. 4, a uniform and clear fluorescent image is observed over a whole measurement range. That is, as a characteristic of the present invention, the very small amount fluorescence reader can be realized in which uniform fluorescent observation is possible without being influenced by the distortion or deflection of the chip or micro array and which is easy in measurement scanning and high in sensitivity. Moreover, the very small amount fluorescence reader of the present invention is also characterized in that the configuration is simple and can inexpensively be achieved.

Moreover, in a comparative example for the present example, the sample was measured by a commercial confocal detector (Packard BioChip Technologies product, Scan Array 4000XL). The same sample as that of the above-described example was used.

Figure 5:
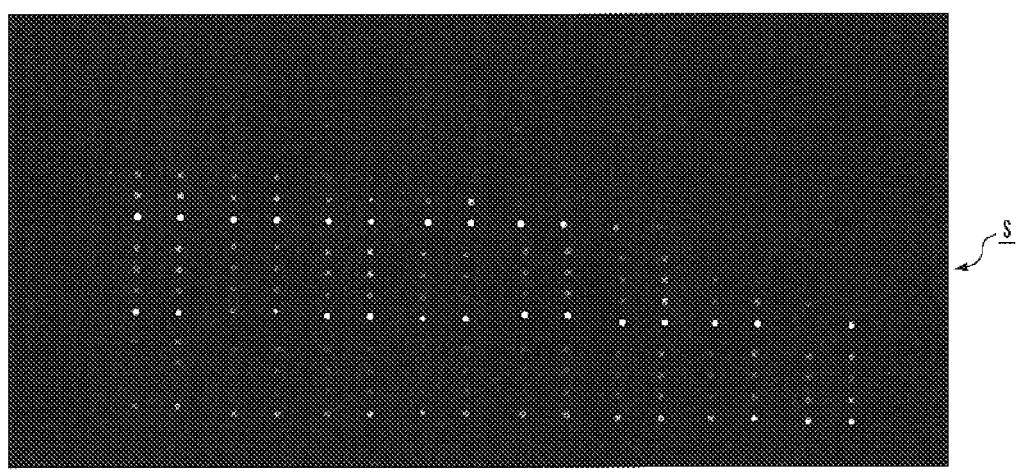
FIG. 5 is a photograph showing the measurement result according to a comparative example of the present invention.

FIG. 5 is a photograph showing the measurement result of the comparative example. As shown in FIG. 5, even on the slide glass S which seems to be flat, a portion that cannot be measured (upper right portion, and the like) remarkably appears by a slight skew in a broad measurement range. This cannot realize an exact inspection. In the confocal detector, since the exciting light is focused in the sample, the quantity of light per unit area before/after the focal point largely changes. Therefore, when the sample even slightly deviates from the focused position by the skews, the intensity of the fluorescence emitted from the sample largely changes. As compared with the comparative example of FIG. 5, the exciting light of the very small amount fluorescence reader according to the present invention shown in FIG. 4 is the parallel luminous flux. Even when the sample deviates from the focal position of the objective lens, the quantity of light per unit area has no change. Accordingly, uniform fluorescent photometry is possible regardless of the skew or deflection. In this manner, an effect of the very small amount fluorescence reader by the present invention is apparent.

It is to be noted that the present invention is not limited only to the above-described embodiment, and can appropriately be modified and practiced without departing from the scope. For the fluorescent read by the present invention, only the above-described sample is not the object, and the measurement object is not limited.

According to the present invention, the following functions are performed.

(1) According to the fluorescence reader of the present invention, when the exciting light is formed into the parallel luminous flux, the quantity of light per unit area becomes constant. Therefore, uniform fluorescent photometry can be carried out without being influenced flatness such as the distortion and deflection of DNA chip or DNA micro array which is the measurement object. Furthermore, the very small amount of fluorescence can be detected from the sample from which only weak fluorescence can be obtained as in coupling reaction of the nucleic acid with high sensitivity, and the exciting light with which the sample is irradiated is formed into the parallel luminous flux having the certain sectional area to configure the optical system in which the sample can be prevented from being damaged.

Moreover, when the simple optical system is employed, a small-sized inexpensive reader can be configured. Furthermore, even when the sample is formed on either side of the carrier with respect to the objective lens, the photometry is possible, and a reader which is easily operated and in which measurement conditions can easily be set can be configured.

(2) According to the fluorescence reader of the present invention, it is possible to adjust an exact focus with respect to the sample by a telecentric excitation optical system.

(3) According to the fluorescence reader of the present invention, fluorescence or disturbance light emitted from the plane other than that of the sample upon which the exciting light is incident can be prevented from reaching photo detection means.

(4) According to the fluorescence reader of the present invention, the shape and diameter of the pinhole can be changed in accordance with the state of the sample or the measurement purpose.

(5) According to the fluorescence reader of the present invention, when the fluorescence from the sample is detected, the fluorescent amount can be measured.

(6) According to the fluorescence reader of the present invention, when the fluorescence from the sample is detected, it is judged whether or not the targeted nucleic acid is present. When the nucleic acid is present, the fluorescent amount can be measured.

(7) According to the fluorescence reader of the present invention, the scanning can be accelerated with respect to a plurality of samples.

According to a fluorescence reader of the present invention, when an exciting light is formed into a parallel luminous flux, a quantity of light per unit area becomes constant. Therefore, even with distortion or deflection in DNA chip or DNA micro array which is a measurement object, uniform fluorescent photometry can be performed. Since a focal depth is large, a fluorescent amount that can be acquired is large, an influence of a background noise is not easily exerted, therefore a very small amount of fluorescence can be detected with high sensitivity, and an SN ratio is enhanced.

Furthermore, since an optical system is simple, it is possible to inexpensively design/manufacture a small-sized reader. When the DNA chip or DNA micro array is only disposed on a stage, and the like, a strict focal point is not required, and it is therefore easy to set conditions of a focusing operation or measurement. The measurement is carried out irrespective of the shape of a carrier. Since a parallel light is used in the exciting light, density of the exciting light with respect to a large plane of the sample or per unit area is reduced, and therefore a fluorescent dyestuff is hardly deteriorated.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A fluorescence reader which detects fluorescence from a sample present on a carrier or in a solution, comprising:

a light source which radiates parallel light;

a projection lens which converges the light from the light source;

an excitation pinhole disposed at a front-side focal position of the projection lens, which shapes the parallel light radiated from the light source;

an objective lens which permits the light converged at a rear-side focal position and radiated onto the sample to pass through the objective lens;

an image forming lens which forms fluorescence emitted from the sample and passed through the objective lens into an image;

a light receiving pinhole disposed at an image forming position of the image forming lens; and a detector which detects the fluorescence passed through the light receiving pinhole, wherein a shape of the excitation pinhole and a diameter of the light receiving pinhole are changeable.

2. The fluorescence reader according to claim 1, wherein a size of the image formed at the image forming position of the image forming lens is substantially equal to that of the light receiving pinholes.

3. The fluorescence reader according to claim 1, wherein the sample comprises a nucleic acid, a reagent coupled with the nucleic acid, and a fluorescent dyestuff coupled with the nucleic acid or the reagent coupled with the nucleic acid.

4. The fluorescence reader according to claim 3, wherein at least a part of the nucleic acid or one or more parts are immobilized on the carrier, and the fluorescent dyestuff is coupled with the reagent peculiarly coupled with the nucleic acid.

5. The fluorescence reader according to claim 1, which further comprises a specimen including the samples arranged at a certain interval on the carrier, and wherein the specimen moves every certain interval, and measuring of the fluorescence and moving of the specimen are repeated to measure a plurality of samples.

* * * * *